United States Patent [19]

Nevens et al.

[11] 4,407,660
[45] Oct. 4, 1983

[54] PLASMAPHERESIS ASSEMBLY AND ASSOCIATED FLUID MANIFOLD

[75] Inventors: Charles Nevens, Barrington; Ronald A. Williams, Mundelein, both of Ill.

[73] Assignee: Baxter Travenol Laboratories, Inc., Deerfield, Ill.

[21] Appl. No.: 300,338

[22] Filed: Sep. 8, 1981

[51] Int. Cl.³ .............................................. A61M 5/00
[52] U.S. Cl. ........................................ 604/6; 604/256; 604/410
[58] Field of Search ............... 128/247, 213 A, 213 R, 128/272, 214 R, 214 D; 251/309, 310, 311, 312; 137/625.41, 625.47; 604/4–6, 32, 33, 248, 249, 256, 410

[56] References Cited

U.S. PATENT DOCUMENTS

| | | | |
|---|---|---|---|
| 2,083,228 | 6/1937 | Geyer | 137/625.41 |
| 2,485,842 | 10/1949 | Pennington . | |
| 2,854,027 | 9/1958 | Kaiser et al. . | |
| 3,048,192 | 8/1962 | Murphy, Jr. . | |
| 3,185,179 | 5/1965 | Harautuneian . | |
| 3,187,750 | 6/1965 | Tenczar, Jr. . | |
| 3,405,706 | 10/1968 | Cinqualbre . | |
| 3,434,473 | 3/1969 | Smith | 128/221 |
| 3,494,351 | 2/1970 | Horn . | |
| 3,618,637 | 11/1971 | Santamieri . | |
| 3,648,693 | 3/1972 | Koremura . | |
| 3,678,960 | 7/1972 | Leibinsohn . | |
| 3,722,502 | 3/1973 | Besuner et al. . | |
| 3,782,382 | 1/1974 | Naftulin . | |
| 3,794,032 | 2/1974 | Derouineau . | |
| 3,834,372 | 9/1974 | Turney . | |
| 3,848,581 | 11/1974 | Cinqualbre et al. . | |
| 3,916,948 | 11/1975 | Benjamin . | |
| 3,918,450 | 11/1975 | Patel | 128/247 |
| 3,945,380 | 3/1976 | Dabney et al. | 128/214 R |
| 3,957,082 | 5/1976 | Fuson et al. . | |
| 3,985,155 | 10/1976 | Nightingale | 251/309 X |
| 3,986,506 | 10/1976 | Garber et al. . | |
| 3,993,099 | 11/1976 | Nightingale | 251/309 X |
| 4,051,852 | 10/1977 | Villari | 128/214 G X |
| 4,126,133 | 11/1978 | Schwartz . | |
| 4,146,055 | 3/1979 | Ryder et al. | 137/625.41 |
| 4,195,631 | 4/1980 | Baucom | 137/625.41 X |
| 4,222,379 | 9/1980 | Smith . | |

FOREIGN PATENT DOCUMENTS 4227772 11/1973 Australia .

OTHER PUBLICATIONS

Fenwal Laboratories brochure showing their Plasmapheresis BLOOD-PACK ® Units.
Fenwal Laboratories brochure showing their BLOOD-PACK ® Units with Integral Donor Tubing.

Primary Examiner—C. Fred Rosenbaum
Assistant Examiner—Michelle N. Lester
Attorney, Agent, or Firm—Paul C. Flattery; Daniel D. Ryan

[57] ABSTRACT

A plasmapheresis assembly includes a fluid manifold which interconnects the phlebotomy needle of the assembly with a pair of blood collection containers. The manifold includes a removably insertable plug member which, when inserted, blocks fluid flow through the manifold to retain anticoagulant solution in the containers prior to use and which, after removal, affords fluid flow through the manifold and permits the attachment of a recipient set to the manifold.

18 Claims, 16 Drawing Figures

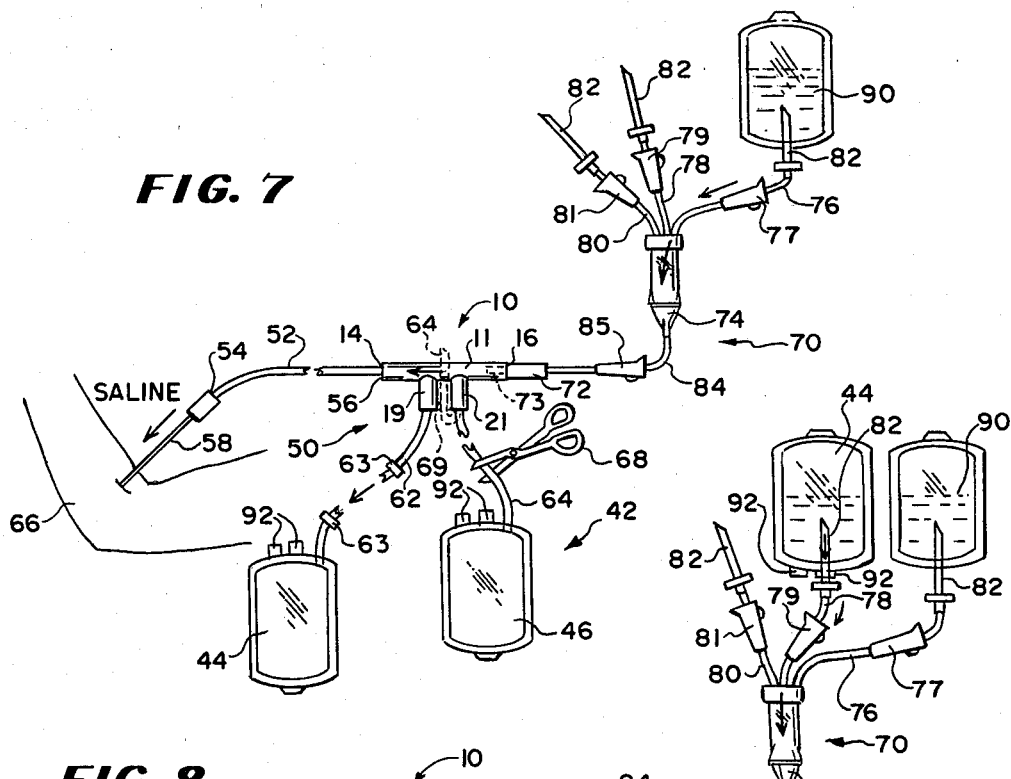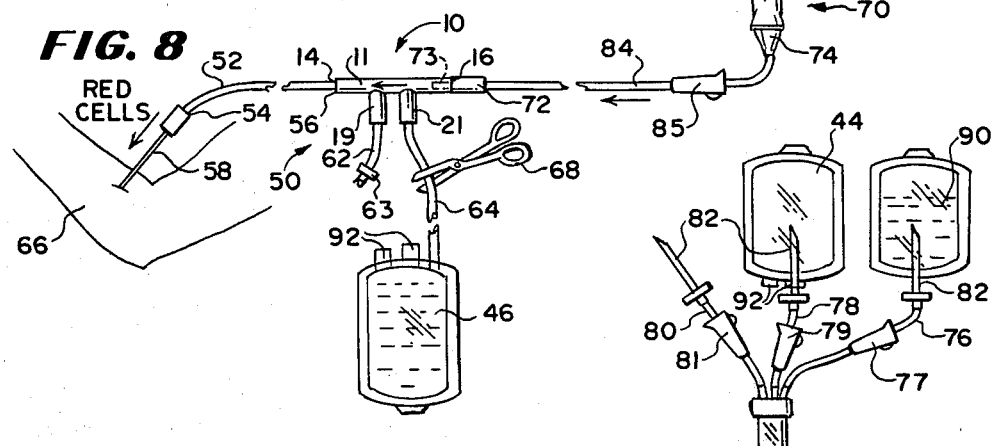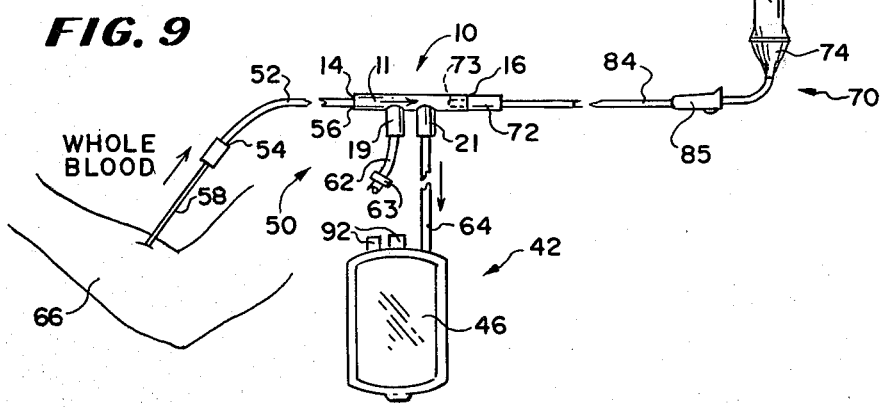

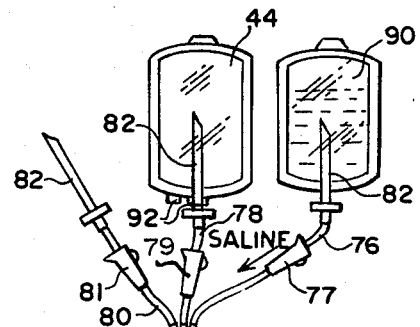
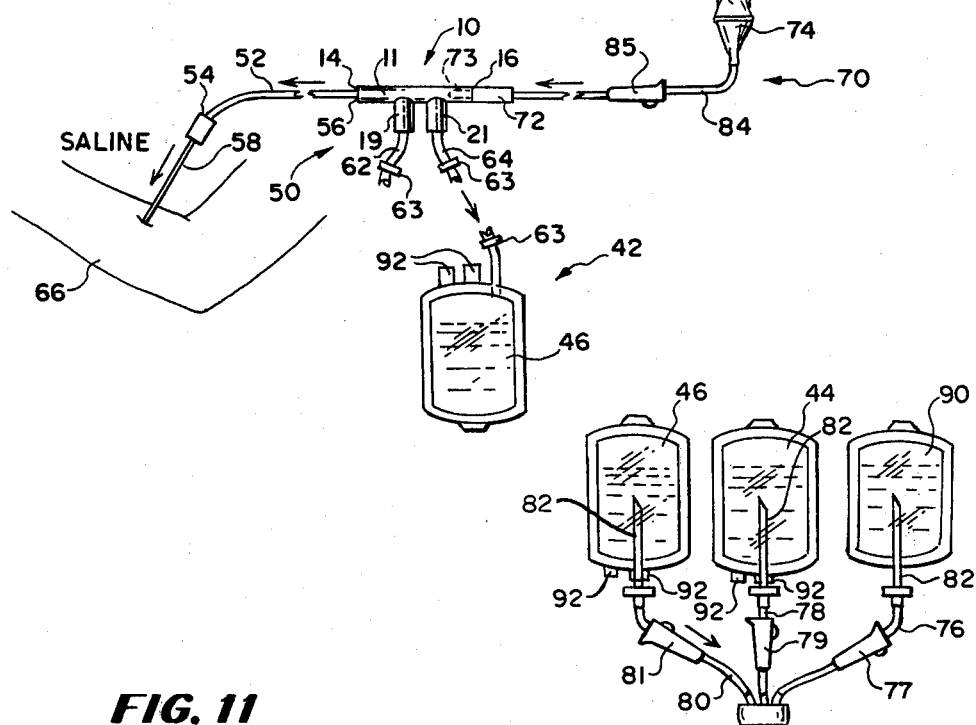
FIG. 10
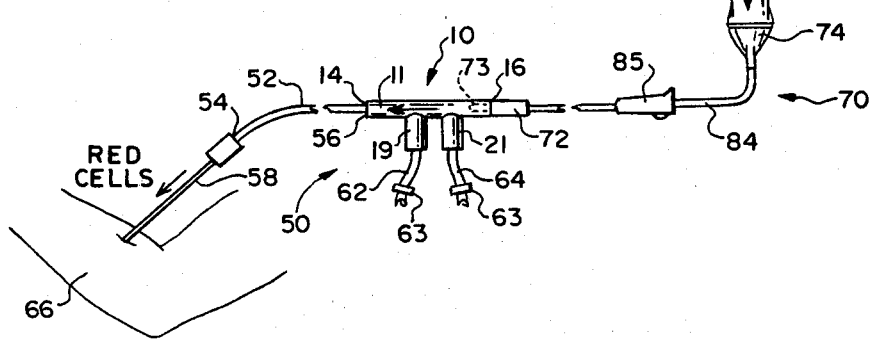
FIG. 11

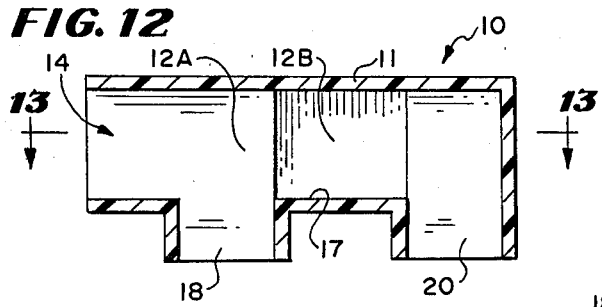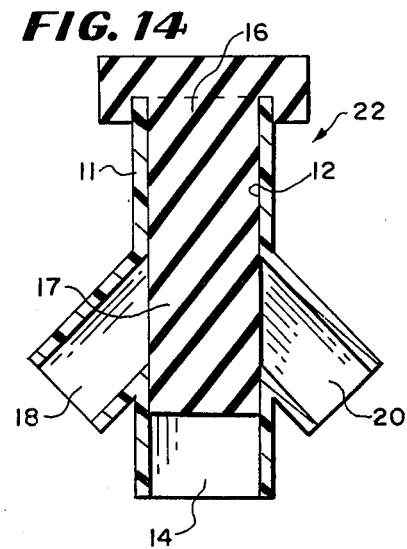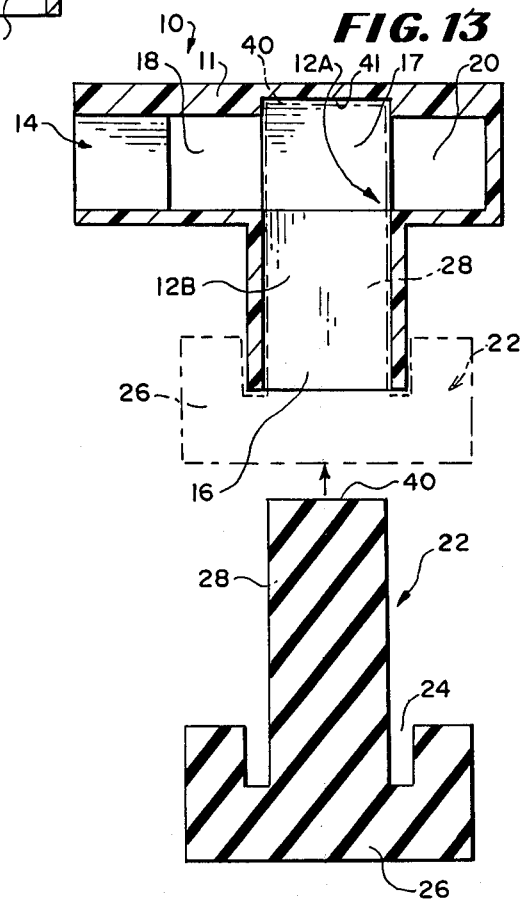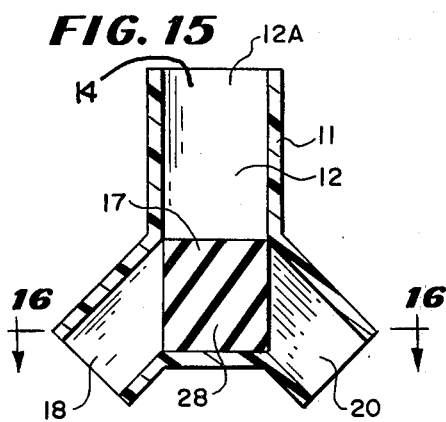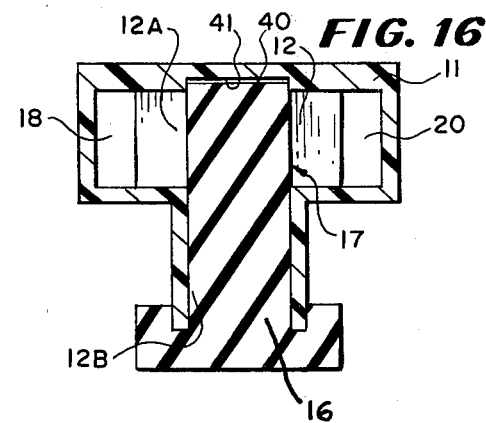

PLASMAPHERESIS ASSEMBLY AND ASSOCIATED FLUID MANIFOLD

FIELD OF THE INVENTION

The invention generally relates to fluid manifolds. The invention also generally relates to plasmapheresis apparatus and processes.

DESCRIPTION OF THE PRIOR ART

Attention is directed to the following United States Patents, which generally concern various fluid flow control devices:

Burbage, U.S. Pat. No. 1,229,029, June 5, 1917
Stern, U.S. Pat. No. 2,796,887, June 25, 1957
Nelson et al, U.S. Pat. No. 2,798,690, July 9, 1957
Kruschik, U.S. Pat. No. 2,856,961, Oct. 21, 1958
Szulc et al, U.S. Pat. No. 2,926,885, Mar. 1, 1960
Ocampo, U.S. Pat. No. 2,970,802, Feb. 7, 1961
Lippig, U.S. Pat. No. 3,089,627, May 14, 1963
Brown, U.S. Pat. No. 3,675,674, July 11, 1972
Smith et al., U.S. Pat. No. 3,694,423, Sept. 29, 1972
Nightingale, U.S. Pat. No. 3,985,155, Oct. 12, 1976
Nightingale, U.S. Pat. No. 3,993,099, Nov. 23, 1976
Douglas et al., U.S. Pat. No. 4,212,322, July 15, 1980
Nightingale, U.S. Pat. No. 4,268,472, May 19, 1981

Attention is also directed to the following United States Patents, which more specifically concern the use of fluid flow control devices in the collection and infusion of parenteral fluids:

Tenczar, U.S. Pat. No. 3,187,750, June 8, 1965
Cinqualbre, U.S. Pat. No. 3,405,706, Oct. 15, 1968
Naftulin, U.S. Pat. No. 3,459,182, Aug. 5, 1969
Horn, U.S. Pat. No. 3,494,351, Feb. 10, 1970
Koremura, U.S. Pat. No. 3,648,693, Mar. 14, 1972
Besuner et al., U.S. Pat. No. 3,722,502, Mar. 27, 1973
Naftulin et al., U.S. Pat. No. 3,782,382, Jan. 1, 1974
Cinqualbre et al., U.S. Pat. No. 3,848,581, Nov. 19, 1974
Patel, U.S. Pat. No. 3,918,450, Nov. 11, 1975
Dabney et al., U.S. Pat. No. 3,945,380, Mar. 23, 1976
Benjamin, U.S. Pat. No. 3,916,948, Nov. 4, 1975
Garber et al., U.S. Pat. No. 3,986,506, Oct. 19, 1976
Schwoboda et al., U.S. Pat. No. 4,181,121, Jan. 1, 1980
Djerassi, U.S. Pat. No. 4,197,847, Apr. 15, 1980
Wingrove, U.S. Pat. No. 4,206,767, June 10, 1980

Plasmapheresis assemblies, which facilitate the collection (or "harvesting") of large volumes of plasma for fractionation purposes, typically employ ball valve arrangements and/or external clamps to control the flow of fluids through the assemblies. For example, the above-cited Naftulin et al and Dabney et al patents each concerns the use of a ball valve arrangement to control fluid flow during a plasmapheresis procedure.

Another example of a known plasmapheresis assembly which employs a ball valve arrangement is shown in FIG. 1. This assembly 1, which is sold by the Fenwal Division of Travenol Laboratories, Inc., includes two containers 2. Any array of flexible tubing 3 communicates with the containers 2 and terminates in a single phlebotomy needle 4. The array includes two inline Y-connectors 8 and 9. One of the Y-connectors (connector 9 in FIG. 1) is adapted to interconnect the assembly 1 with a conventional recipient set during the course of the plasmapheresis procedure.

In the assembly shown in FIG. 1, as well as in plasmapheresis assemblies in general, each of the containers 2 is partially prefilled with an anticoagulant solution 5 during the manufacturing process. The presence of the solution 5 prevents the formation of blood clots during the course of the plasmapheresis procedure. To retain the desired amount of anticoagulant solution 5 in each container 2 prior to initiation of the procedure, a ball valve in the form of a stainless steel bead 6 is located within the tubing 3 at the junction between the tubing 3 and each container 2.

During the course of the plasmapheresis procedure, the bead 6 associated with each container 2 is manually squeezed out of the tubing 3 and into the associated container 2 to open fluid flow communication with the container 2.

Use of beads, or ball valves, in similar contexts is also shown in the above-cited Tenczar, Koremura, Benjamin, and Garber et al patents.

Instead of using internally mounted beads 6, other known plasmapheresis assemblies employ a ball valve in the form of a molded plug at the junction of the tubing 3 and each container 2.

Alternately, instead of using internally mounted ball valves and the like, external clamps 7 (shown in phantom lines in FIG. 1) can close the tubing 3 upstream of each container 2 to retain the desired amount of anticoagulant solution 5 in each container 2 prior to use and to subsequently control fluid flow communication with the containers 2.

The internally mounted ball valve arrangements or the externally mounted clamps as just described necessitate additional steps, frequently manually performed, during the manufacture of plasmapheresis assemblies. Such fluid flow devices only complicate the manufacturing process and increase the overall cost of the assemblies.

Such assemblies also must typically include a plurality of inline Y-connectors to interconnect the containers with a single phlebotomy needle and to provide for the interconnection of the assembly itself with a recipient set and the like when desired. Like the ball valves and clamps, the multiple Y-connectors only add to the complexity of the fluid circuit associated with the assembly and increase the overall cost.

One of the principal objects of this invention is to provide a fluid manifold which can serve to replace conventional ball valve arrangements, plugs, and external clamps in plasmapheresis assemblies in retaining anticoagulant solution in the blood collection containers prior to the start of the blood collection procedure and in controlling fluid flow communication with the containers during the course of the procedure.

Another principal object of this invention is to provide a fluid manifold which can also serve as a site for the interconnection of a plasmapheresis assembly and the like with a recipient set.

Still another principal object of this invention is to provide a fluid manifold which serves to reduce the overall complexity of the fluid circuit utilized to interconnect blood collection containers with a single phlebotomy needle.

Yet another principal object of this invention is to provide a fluid manifold which facilitates the construction of a plasmapheresis assembly and the like in an efficient and cost effective manner.

SUMMARY OF THE INVENTION

To achieve these and other objects, the invention provides a fluid manifold which comprises a main passage having first and second portions, each of which is normally open to the atmosphere and can be attached to a source of fluid. A pair of branch passages communicates with the main passage. Plug means is removably insertable into the one of the normally open portions of the main passage to sealingly close that portion. At the same time, the plug means serves to block fluid flow between the branch passages through the main passage. The manifold can be utilized to interconnect two or more containers with a source of fluid, without an overly convoluted fluid path array. The manifold can also be utilized to selectively control fluid flow communication between the containers.

In one embodiment, when the plug means is inserted into the main passage, the fluid flow between the main passage and only one of the branch passages is blocked. The flow of fluid between the main passage and the other branch passage is unaffected. By virtue of this arrangement, fluid entering the main passage through the first portion thereof is channeled exclusively into the other branch passage.

The invention also provides a plasmapheresis assembly which includes the above described fluid manifold. In this arrangement, the assembly includes a pair of blood collection containers attached in flow communication with the branch passages of the manifold, and a phlebotomy needle which is coupled via flexible tubing with the other normally open portion of the main passage. A straightforward interconnection of the containers with a single phlebotomy needle is thus achieved by use of the manifold. Furthermore, when the plug means is inserted into the main passage, the intermixing of anticoagulant between containers prior to the start of the plasmapheresis procedure is prevented. Removal of the plug means permits the interconnecting of a recipient set with the assembly through the manifold. The manifold can also assist in facilitating the proper sequence of operative steps during the subsequent course of the procedure.

The manifold which embodies the features of the invention lends itself to relatively inexpensive manufacturing techniques and promotes the construction of the plasmapheresis assembly in an efficient and cost effective manner.

Other features and advantages of the invention will be pointed out in, or will be apparent from, the specification and claims, as will obvious modification of the embodiments shown in the drawings.

DESCRIPTION OF THE DRAWINGS

FIGS. 6 through 11 are a series of partially diagrammatic views of the sequence of a plasmapheresis procedure utilizing the plasmapheresis assembly shown in FIGS. 2 and 4;

FIG. 12 is an enlarged section view of an alternate embodiment of a fluid manifold which embodies various of the features of the invention;

FIG. 13 is an exploded section view of the fluid manifold taken generally along line 13—13 in FIG. 12;

FIG. 14 is an enlarged section view of another alternate embodiment of a fluid manifold which embodies various of the features of the invention;

FIG. 15 is an enlarged section view of another alternate embodiment of a fluid manifold which embodies various of the features of the invention; and FIG. 16 is a section view of the manifold taken generally along line 16—16 of FIG. 15.

Before explaining the embodiments of the invention in detail, it is to be understood that the invention is not limited in its application to the details of construction and the arrangement of components as set forth in the following description or as illustrated in the accompanying drawings. The invention is capable of other embodiments and of being practiced or carried out in various ways. Furthermore, it is to be understood that the phraseology and terminology employed herein is for the purpose of description and should not be regarded as limiting.

DESCRIPTION OF THE PREFERRED EMBODIMENT

Figure 3:
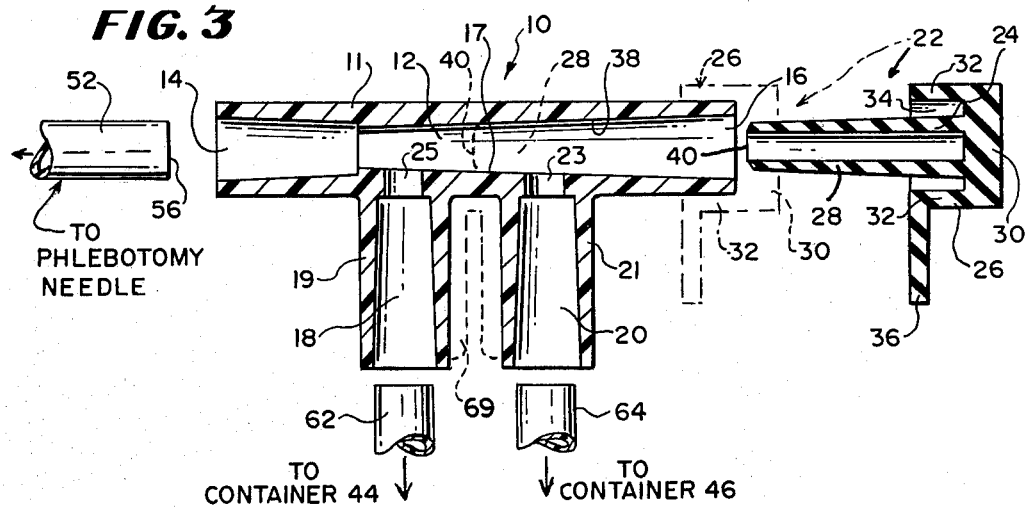
FIG. 3 is an enlarged and exploded section view of the fluid manifold shown in FIG. 2.

A fluid manifold 10 which embodies various of the features of the invention is shown in FIG. 3. In general construction, the manifold 10 includes a main body 11 through which a main passage 12 extends. The main passage 12 has spaced first and second portions, respectively 14 and 16, each of which is normally open to communication with the atmosphere and accommodates independent attachment to a desired source of fluid. In the embodiment shown in FIG. 3, the first and second portions 14 and 16 comprise oppositely axially spaced open ends of the main passage.

Still referring principally to FIG. 3, a pair of branch passages 18 and 20 communicates with the main passage 12. One branch passage 18 (hereinafter referred to as the first branch passage) is generally adjacently disposed to the first normally open end 14. The other branch passage 20 (hereafter referred to as the second branch passage) is generally adjacently disposed to the second normally open end 16.

By virtue of this construction, the main passage 12 includes an intermediate portion 17 which defines a fluid path between the branch passages 18 and 20.

In the illustrated embodiment, each branch passage 18 and 20 extends within a tubular body, respectively 19 and 21. The tubular bodies 19 and 21 extend outwardly from the same side of the main body 11, and the branch passages 18 and 20 are each generally parallel to one another and generally perpendicularly disposed relative to the main passage 12.

The manifold 10 as heretofore described lends itself to relatively efficient and economical manufacturing techniques. For example, in the illustrated embodiment, the main body 11 and tubular bodies 19 and 21 of the manifold 10 are injected molded as an integral unit from a rigid or semi-rigid plastic material, such as polycarbonate, polyvinyl chloride, or acrylic.

To control fluid flow into and through the main passage 12 and associated branch passages 18 and 20, the manifold 10 includes plug means 22 which is removably insertable into one of the normally open ends of the main passage 12. As shown in phantom lines in FIG. 3, in the illustrated embodiment, the plug means 22 is insertable into the second open end 16 and extends axially into the intermediate fluid path portion 17 in a direction which is generally parallel to the fluid flow between the branch passages 18 and 20. As will soon be described in greater detail, when inserted, the plug means 22 serves to sealingly close the end 16 while simultaneously blocking flow communication through the fluid path 17 between the first and second branch passages 18 and 20.

While various constructions are possible, in the illustrated embodiment (see FIG. 3), the plug means 22 takes the form of a plug member 24 having a cap portion 26, which is formed to fit snugly about the exterior of the second end 16, and a stem portion 28, which is formed to extend axially into the main passage 12.

More particularly, the cap portion 26 includes an end wall 30 and a circumferentially depending sidewall 32. The sidewall 32 encircles an open area 34 within the cap portion 34. The area 34 has an inner diameter generally equal to the exterior diameter of the second end 16.

By virtue of this construction, and as shown in phantom lines in FIG. 3, the cap portion 26 fits snugly in a fluid tight relationship over the second end 16, with the sidewall 32 surrounding the exterior of the second end 16 and, together with the end wall 30, sealingly closing the second end 16.

In the illustrated and preferred embodiment, the cap portion 26 includes a tab 36 which extends at a right angle outwardly from one edge of the sidewall 32. The tab 36 can be readily grasped between the fingers of the operator and a force parallel to the axis of the main passage 12 exerted to remove the cap portion 26 from its snug engagement on the end 16. Attachment of the end 16 to an external source of fluid is thereby permitted.

The stem portion 28 of the plug member 24 extends from the interior surface of the end wall 30 through and beyond the open area 34 in a direction generally parallel to the fluid flow through the path 17. The stem portion 28 has an outside diameter accommodating a fluid tight, interference fit within the main passage 12 (as shown in phantom lines in FIG. 3).

In the illustrated and preferred embodiment, the main passage 12 includes an axially inwardly tapered portion 38 (see FIG. 3) which extends from the second end 16 toward the first end 14 and which includes the fluid path portion 17. The stem portion 28 is correspondingly tapered inwardly away from the end wall 30. The matching tapers of the stem portion 28 and main passage portion 38 facilitate the insertion of the stem portion 28 into the main passage 12 and the formation of the interference fit between the main passage portion 38 and the stem portion 28. It should be noted that, in the illustrated and preferred ambodiment, this interference fit is complete only when the cap portion 26 is likewise completely disposed in its fluid tight fit over the second end 16 of the main passage 12.

The plug member 24, like the main body 11 and tubular bodies 19 and 21 of the manifold 10, lends itself to relatively efficient and economical manufacturing techniques. For example, the plug member 24 can be fabricated by injection molding from a rigid or semi-rigid plastic material, such as polycarbonate, polyvinyl chloride, or acrylic. Or the plug member 24 can be made utilizing a compression molding process from a resiliently compressible material, such as natural rubber. This latter construction is preferred because it further promotes the tight, interference fit of the stem portion 28 within the main passage portion 38 and of the cap portion 26 about the second end 16.

When a resiliently compressible material is used, the maximum outside diameter of the stem portion 28 adjacent to the end wall 30 is also preferably slightly larger than the interior diameter of the passage portion 38 adjacent to the end 16. This further enhances the snug, fluid tight fit of the plug member 24 on the end 16.

As can be seen in phantom lines in FIG. 3, when the cap portion 26 sealingly closes the second end 16, the stem portion 28 is fully inserted in its interference fit within the main passage portion 38. When fully inserted, the stem portion 28 extends into the fluid path portion 17 in a sealing relationship across the entirety of the junction 23 of the second branch passage 20 with the main passage 12. However, at the same time, the terminal end 40 of the stem portion 28 is spaced away from the corresponding junction 25 between the first branch passage 18 and the main passage 12.

By virtue of this construction, when the stem portion 28 is fully inserted in its interference fit within the main passage portion 28, flow communication between the second branch passage 20 and the main passage 12 is blocked. Flow communication through the main passage 12 between the first and second branch passages 18 and 20 is thereby prevented, as is the leakage of fluid out of the second end 16.

However, at the same time, flow communication between the first branch passage 18 and the main passage 12 is afforded. Thus, when fully inserted, the plug member 24 effectively channels all fluid introduced through the first open end 14 into the main passage 12 exclusively into the first branch passage 18.

It should be appreciated that the fluid manifold 10 as heretofore described with reference principally to FIG. 3 can be variously constructed. Various alternate constructions which embody the features of the invention are shown in FIGS. 12 through 16. Components which are common to the heretofore described FIG. 3 embodiment are assigned common reference numerals.

In the alternate embodiment of the manifold 10 shown in FIGS. 12 and 13, the main body 11 is configured to form a generally T-shaped main passage (as best seen in FIG. 13) having perpendicularly intersecting legs designated 12A and 12B. The first open portion 14 comprises the end of the leg 12A, and the second open portion 16 comprises the end of the leg 12B.

In this embodiment, the first and second branch passages 18 and 20 communicate with the leg 12A on either side of its intersection with the leg 12B. The branch passages 18 and 20 extend in a side-by-side relationship from the leg 12A at generally at right angle relative to the axis of both of the legs 12A and 12B. The fluid path 17 between the branch passages 18 and 20 thus extends directly across the junction of the leg 12B with leg 12A.

In this arrangement, the plug means 22 is removably insertable into the open end 16 of the leg 12B and extends axially across the fluid path 17 in a direction which is generally transverse of the fluid flow between the branch passages 18 and 20. More particularly, the cap portion 26 of the plug means 22 fits snugly about the exterior of the second end 16 to seal that end 16 (as shown in phantom lines in FIG. 13), while the associated stem portion 28 extends in an interference fit relationship within the leg 12B and in a blocking relationship across the fluid path 17 (see FIG. 13). The terminal end 40 of the stem portion 28 is preferably positioned in sealing relationship within a notch 41 formed within the leg 12A opposite to the junction of the legs 12A and 12B.

In the FIGS. 12 and 13 embodiment, as in the embodiment shown in FIG. 3, when the stem portion 28 is fully inserted in its interference fit within the leg 12B, flow communication between the second branch passage 20 and the end 14 of the main passage is blocked, while flow communication between the first branch passage 18 and the end 14 is afforded.

Reference is now made to the alternate embodiment shown in FIG. 14. In this embodiment, and like the embodiment shown in FIG. 3, the first and second portions 14 and 16 of the main passage 12 are oppositely axially spaced. However, unlike the FIG. 3 embodiment, the branch passages 18 and 20 extend from opposite sides of the main passage 12 and at acute angles thereto.

It should be appreciated that the particular angular relationship of the branch passages 18 and 20 in any of the embodiments ultimately depends upon the particular use contemplated for the manifold 10.

In this arrangement, the plug means 22 removably is inserted into the second end 16 and extends axially into the fluid path 17 between the branch passages 18 and 20 in a direction which is generally transverse of the fluid flow between the branch passage 18 and 20. Unlike the embodiments heretofore discussed, the plug means 22 simultaneously blocks flow communication between the main passage 12 and both branch passages 18 and 20.

It should thus be appreciated that, by varying the relative alignment of the branch passages 18 and 20 along the main passage 12 in any of the embodiments, one or both of the branch passages 18 and 20 can be selectively blocked by the plug means 22.

In the alternate embodiment shown in FIGS. 15 and 16, the main passage has generally perpendicularly intersecting legs 12A and 12B, with the first open portion 14 comprising the end of the leg 12A, and the second open portion 16 comprising the end of the leg 12B. The branch passages 18 and 20 extend from opposite sides from the leg 12A and at acute angles thereto.

In this embodiment, and like the FIGS. 12 and 13 embodiment, the plug means 22 is removably inserted into the end 16 and extends axially through the leg 12B and into the fluid path 17 in a direction generally transverse of the fluid flow between the branch passages 18 and 20. As in the FIGS. 12 and 13 embodiment, a notch 41 is provided in the leg 12A into which the terminal end 40 of the stem portion 28 can be positioned.

From the foregoing, it should be appreciated that the manifold 10 may be variously configured to provide different relative arrangements of the open portions 14 and 16 of the main passage 12, as well as different arrangements of the branch passages 18 and 20 relative to each other and relative to the main passage 12. Furthermore, the direction of insertion of the plug means 22, whether axially parallel to or transverse of the flow path 17, may also be varied to suit the operative requirements of the contemplated use.

It should be appreciated that the manifold 10 shown in FIGS. 3 and 12 through 16 is applicable for use in association with various fluid conduction assemblies in which it is desirable to interconnect one or more fluid passages and to control fluid communication between the containers. However, as will soon become apparent, the manifold 10 is particularly well-suited for use in association with a plasmapheresis assembly 42.

In further discussion of the use of the manifold in this environment, reference will be made principally to the manifold embodiment of FIG. 3, although the adaptability of the other manifold embodiments of FIGS. 12 through 16 should be appreciated.

Figure 1:
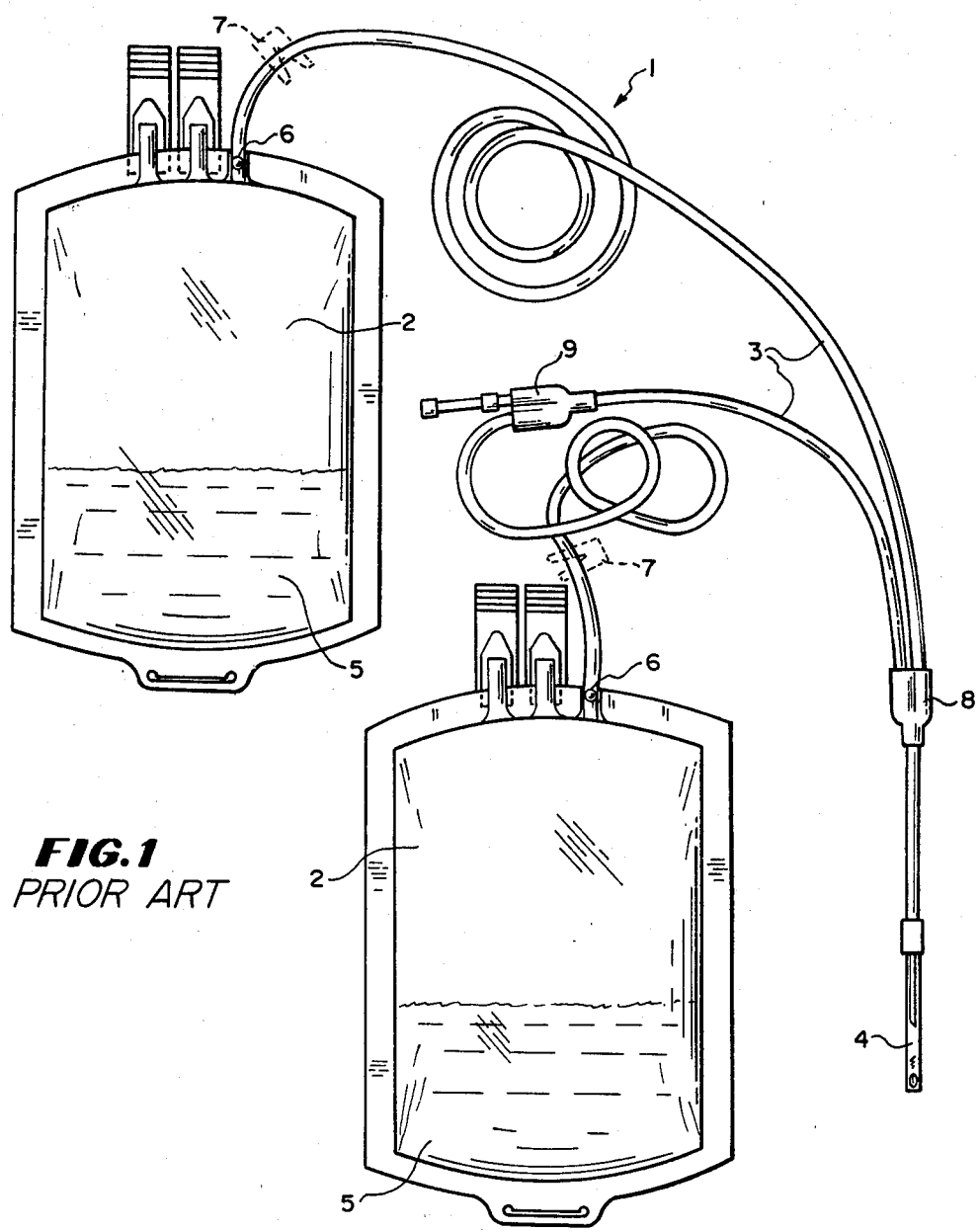
FIG. 1 is a plan view of a conventional plasmapheresis assembly.
Figure 2:
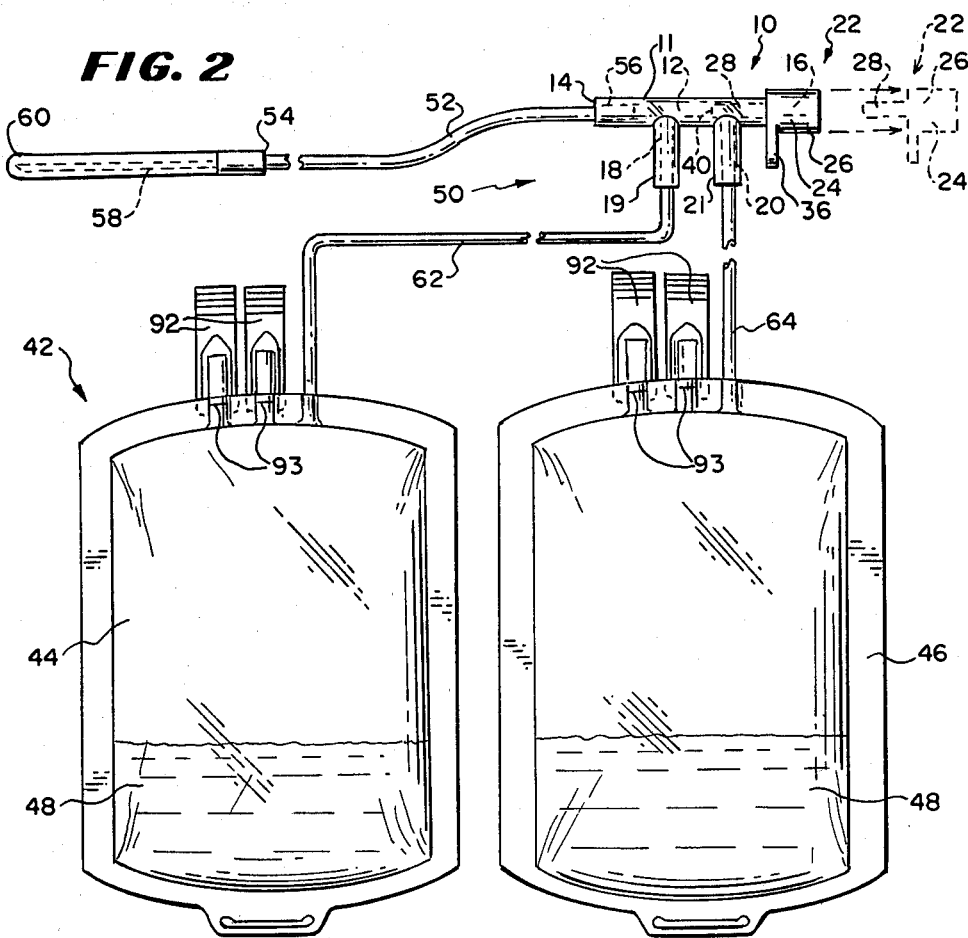
FIG. 2 is a plan view of a plasmapheresis assembly which includes a fluid manifold which embodies various of the features of the invention.

In this environment, as can be seen in FIG. 2, the plasmapheresis assembly 42 includes first and second whole blood collection containers, respectively 44 and 46. The containers 44 and 46 typically take the form of bags fabricated from a plasticized medical grade polyvinyl chloride material.

To prevent blood clotting during the course of the plasmapheresis procedure, the containers 44 and 46 are each preferably prefilled with a predetermined amount of an anticoagulant solution 48, such as ACD. Typically, when a 500 ml container is utilized, approximately 75 ml of anticoagulant solution should be provided.

The assembly 42 also includes conduit means 50 for conducting blood and other parenteral fluids into the containers 44 and 46. Like the containers 44 and 46, the conduit means 50 typically takes the form of flexible tubing fabricated from a medical grade polyvinyl chloride plastic.

In the illustrated embodiment, and still referring principally to FIG. 2, the conduit means 50 includes a length of flexible tubing 52 having opposite end portions 54 and 56. This length of tubing 52 will hereafter be referred to as the primary tubing of the assembly 42.

A phlebotomy needle 58 is attached in flow communication with the end portion 54 of the primary tubing 52. A removable needle cover 60 of conventional construction (see, for example, Bellamy, Jr., U.S. Pat. No. 3,123,072) normally seals the needle 58 from communication with the atmosphere until venipuncture is made. The cover 60 also prevents the loss of anticoagulant solution through the phlebotomy needle 58 prior to venipuncture.

The other end portion 56 of the primary conduit means 52 is bonded, such as by solvent sealing, within the first end 14 of the manifold main passage 12, thereby interconnecting the main passage 12 with the phlebotomy needle 58.

The conduit means 50 also includes first and second auxiliary tubing 62 and 64 which respectively communicate with the containers 44 and 46. The first and second auxiliary tubing 62 and 64 are also attached in flow communication with the respective first and second branch passages 18 and 20 of the manifold 10, such as by solvent sealing.

The manifold 10 thus serves to interconnect both of the containers 44 and 46 of the assembly 42 in flow communication with the single phlebotomy needle 58 in a straightforward and nonconvoluted manner.

When the plug member 24 is positioned on the second end 16 of the main passage 12 (as shown in solid lines in FIG. 2 and in phantom lines in FIG. 3), the cap portion 26 sealingly closes the second end 16, and the stem portion 28 sealingly closes the second container 46 from communication with the main passage 12. The plug member 24 thus seals the second container 46 from communication with the atmosphere, the first container 44, and the phlebotomy needle 58. However, at the same time, communication between the phlebotomy needle 58 and the first container 44 through the primary tubing 52 and main passage 12 is unimpeded.

With the plug member 24 so positioned, the manifold 10 initially serves to prevent the loss or intermixing of anticoagulant solution 48 between the first and second containers 44 and 46. The plug member 24 thus retains the desired amount of anticoagulant solution 48 in each container 44 and 46 prior to the commencement of the plasmapheresis procedure.

Figure 6:
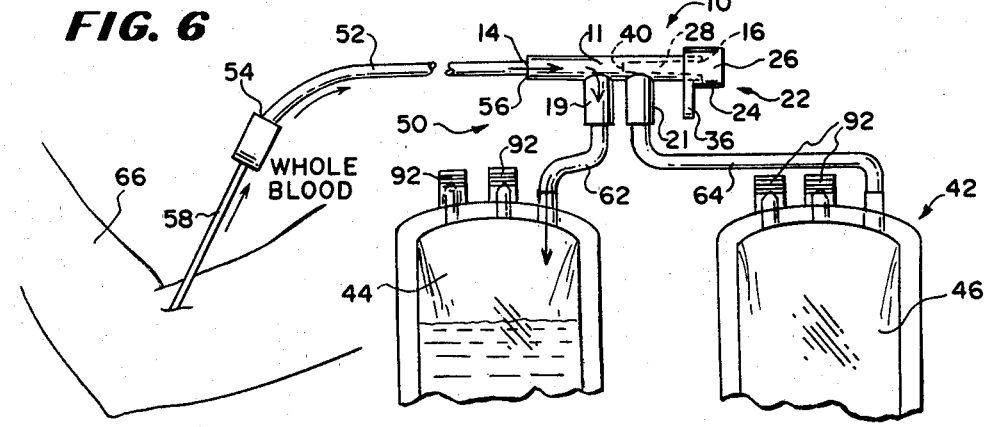

When it is time to begin the plasmapheresis procedure, no change in the operative position of the plug member 24 need be made. As shown in FIG. 6, after removing the needle cover 60, the venipuncture can be made. Whole blood (shown by arrows in FIG. 6) flows from the donor 66, through the primary tubing 52, and into the main passage 12. The fully inserted plug member 24 continues to block all flow communication between the main passage 18 and the second container 46 and prevents leakage of blood from the second end 16. As a result, all of the whole blood drawn from donor 66 is channelled by the plug member 24 into the first container 44.

As is next shown in FIG. 7, after a unit of whole blood has been collected in the first container 44, the first auxiliary tubing 62 is sealed closed, such as by the use of a spaced-apart pair of hand seal clips 63 or by the formation of a hermetic, snap-apart seal using a HEMATRON® dielectric sealer (not shown), sold by the Fenwal Division of Travenol Laboratories, Inc. The auxiliary tubing 62 is thereafter severed between the hand seal clips 63 or along the snap-apart seal, and the first container 44 is separated from the assembly 42.

The first container 44 is placed in a centrifugation device (not shown) to separate the whole blood into plasma and red cells.

During the time the whole blood in the first container 44 is being processed, it is desirable to introduce a flow of saline or similar I.V. solution through the main passage 12 and primary tubing 52 to flush traces of blood from the flow paths 12 and 52 and to maintain the patency of the needle 58. The manifold 10 readily accommodates this next step in the plasmapheresis procedure in a quick and virtually foolproof manner.

More particularly, and as shown in FIG. 7, a clamp or hemostat 68 is placed inline with the second auxiliary tubing 64, to temporarily block the fluid path to the second container 46.

Alternately, the manifold 10 can itself include an integrally formed clamping portion in the form of a slot 69 molded between the members 19 and 21. The slot 69 is shown in phantom lines in FIGS. 3 and 7. A section of the auxiliary tubing 64 can be crimped and inserted into the slot 69 (as shown in phantom lines in FIG. 7) to temporary close the fluid path to the second container 46.

Figure 4:
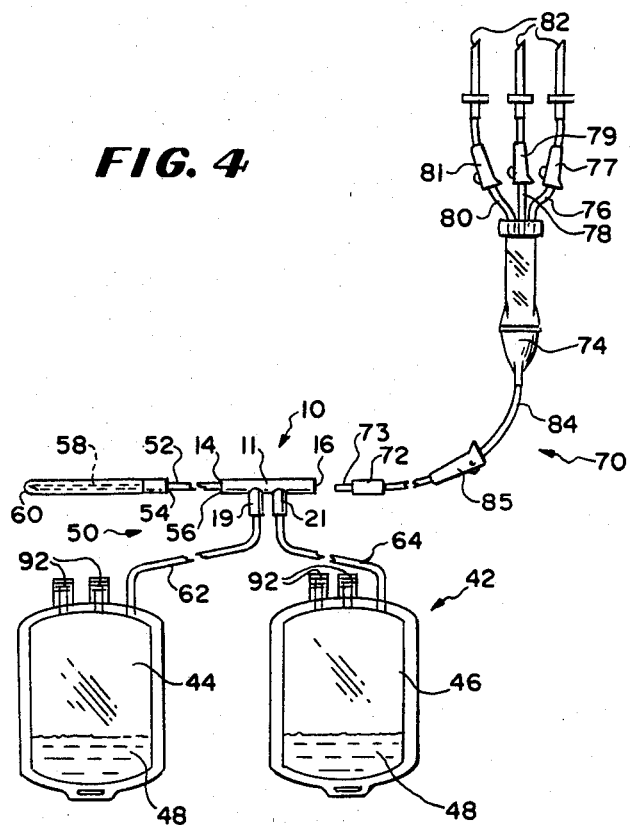
FIG. 4 is a plan view of the plasmapheresis assembly shown in FIG. 2, with the plug member associated with the fluid manifold removed so that a conventional recipient set can be coupled to the assembly.
Figure 5:
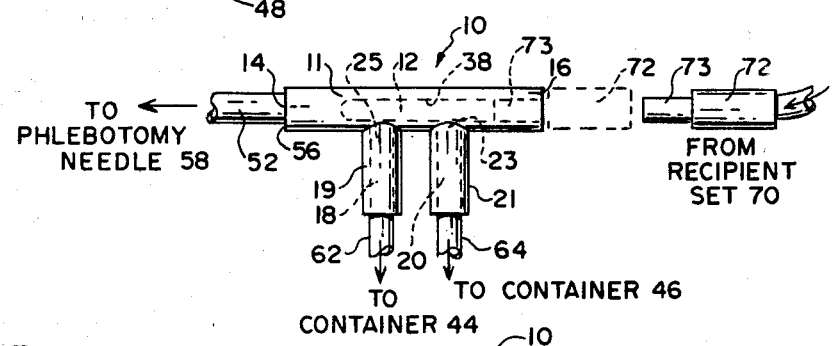
FIG. 5 is an enlarged view of the fluid manifold shown in FIG. 4 with the plug member removed to accommodate the attachment of the recipient set to the manifold.

The plug member 24 can now be removed to open the second end 16. The open second end 16, in turn, readily accommodates the connection of a recipient set 70 to the assembly 42 (see also FIGS. 4, 5, and 7).

The recipient set 70 can be variously constructed. However, in the illustrated embodiment (and see, in particular, FIG. 4), the recipient set 70 includes a combination filter and drip chamber 74. Upstream of the filter/drip chamber 74 are three individual inlet lines 76, 78, and 80, each having a spiked end portion 82. Roller clamps 77, 79, and 81 are provided inline with the inlet lines 76, 78, and 80 to control the fluid flow therethrough. Downstream of the filter/drip chamber 74 is an outlet line 84 and an associated roller clamp 85.

Means 72 is provided for connecting the recipient set 70 to the second open end 16 of the main passage 12 after the plug member 24 has been removed. As can best be seen in FIG. 5, the means 72 takes the form of a coupling member which can be easily fabricated to include a tapered end portion 73 which, like the stem portion 28 of the plug member 24, is insertable in an interference fit relationship into the main passage 12 through the second end 16. However, unlike the stem portion 28, the end portion 73 of the member 72 is purposely sized to occupy only a part of the inwardly tapered portion 38 of the main passage 12 intermediate the junction 23 of the second branch passage 20 and the second end 16.

Referring to FIG. 7, with all of the roller clamps 77, 79, 81, and 85 associated with the recipient set 70 initially closed, the spiked end portion 82 of one of the inlet lines 76 is inserted into the outlet port of a conventional saline (or other I.V.) solution container 90. The roller clamps 77 and 85 are then opened to prime the filter/drip chamber 74 and establish a flow of saline from the container 90 into the donor's arm through the manifold main passage 12 and primary tubing 52. The flow of saline to the donor 66 is shown by arrows in FIG. 7.

The plasmapheresis procedure utilizing the assembly 42 shown in FIG. 2 may, if desired, commence utilizing a different sequence of steps than that heretofore discussed and shown in FIG. 6. In this alternate procedure, which is not shown, the plug member 24 of the manifold 10 is removed prior to venipuncture. The coupling member 72 of the recipient set 70 is then immediately inserted in its place. In this alternate procedure, all of the clamps 77, 79, 81, and 85 associated with the recipient set 70 are initially closed, and the spiked end portion 82 of the inlet line 76 is inserted in the saline container 90.

Still prior to venipuncture, a hemostat is placed inline with each of the first and second auxiliary tubing 62 and 64, thereby temporarily blocking the fluid paths to both containers 44 and 46. The venipuncture is now made, and the hemostat associated with the first container 44 is removed to allow blood to enter the container 44.

In the alternate procedure, as in the first described procedure, a unit of whole blood is collected in the first container 44, and the first auxiliary tubing 62 is sealed and severed to separate the container 44 for processing. The roller clamps 77 and 85 are then opened to flush the main passage 12 and priming tubing 52 with saline. At this point in the alternate procedure, the configuration of the assembly 42 is identical to that shown in FIG. 7.

Regardless of the particular initial sequence of steps taken in the procedure to lead to the disposition of the assembly 42 shown in FIG. 7, the whole blood in the severed-away first container 44 is separated by centrifugation into red cells and a unit of plasma. The unit of plasma is expressed from the container 44 by known manual or automatic methods and collected for fractionation.

The manifold 10 readily accommodates the remaining steps in the plasmapheresis procedure without further change in its operative configuration shown in FIG. 7. As shown in FIG. 8, the spiked end portion 82 of another one of the inlet lines 78 is inserted into an outlet port 92 of the first container 44, which now contains only red cells. As can be seen in FIG. 2, the outlet ports 92 of each container 44 and 46 includes a normally closed membrane 93 which is pierced by the spiked end portion 82 to open the port 92.

The roller clamp 77 is closed to terminate the flow of saline. The roller clamp 79 is opened, and red cells are returned to the donor 66 from the container 44 through the main passage 12 and primary tubing 52. The flow of red cells to the donor 66 is shown by arrows in FIG. 8.

After the red cells in the first container 44 have been returned to the donor 66, the heretofore opened roller clamp 79 (controlling red cell flow) is closed, and the heretofore closed roller 77 (controlling saline flow) is opened to gain flush traces of red cells from the main passage 12 and primary tubing 52.

The next step in the plasmapheresis procedure is shown in FIG. 9. The roller clamps 77 and 85 are both closed to terminate the flow of saline into the main passage 12 and to prevent a backflow of fluids from the main passage 12 into the filter/drip chamber 74. The hemostat 68 heretofore blocking fluid flow through the second auxiliary tubing 64 is removed. As shown by arrows in FIG. 9, whole blood again flows from the donor 66, this time through the main passage 12 of the manifold 10 and into the second container 46.

After whole blood has been collected in the second container 46, the second auxiliary tubing 64 is sealed closed by the use of a pair of hand seal clamps 63 or the formation of hermetic, snap-apart seal. The second auxiliary tubing 64 is severed at the closure point to separate the second container 46 from the assembly 42 for processing (see FIG. 10).

As is shown in FIG. 10, while the whole blood in the separated second container 46 is being processed, the roller clamps 77 and 85 are again opened to allow a flow of saline through the main passage 12 into the donor's arm. During processing, the red cells and plasma in the second container 46 are separated and the plasma expressed. This constitutes the second unit of plasma collected by the assembly 42 using a single phlebotomy.

The final step of the procedure begins. As shown in FIG. 11, the spiked end portion 82 of the remaining inlet line 80 is inserted into an outlet port 92 of the second container 46, thereby opening the associated membrane 93. The red cells in the second container 46 are returned to the donor 66 by opening the appropriate roller clamp 81 (controlling red cell flow) and closing roller clamp 77 (terminating the flow of saline). The flow of red cells to the donor 66 is shown by arrows in FIG. 11. The plamsapheresis procedure utilizing the assembly 42 is then concluded.

From the foregoing discussion, it should be appreciated that the manifold 10 as heretofore described serves to interconnect the containers 44 and 46 with the phlebotomy needle 58 and to maintain the proper levels of anticoagulant solution in each container 44 and 46 prior to use. The manifold 10 can also serve to facilitate the orderly progression of the plasmapheresis procedure itself including the quick and virtually instantaneous connection of the recipient set 70 to the assembly 42.

The manifold 10 lends itself to construction using known injection molding techniques. Furthermore, the manifold 10 simplified the interconnection of tubing and containers, and leads to a straightforward, non-convoluted fluid system associated with the plasmapheresis assembly. Of important note is that the manifold 10 completely obviates the necessity for internal beads, internal plugs, or external clamps to retain anticoagulant prior to use. The manifold 10 thereby significantly facilitates the efficient and cost effective manufacture of the plasmapheresis assembly.

Various of the features of the invention are set forth in the following claims.

We claim:

1. A blood collection assembly comprising
primary conduit means including, at one end thereof, a phlebotomy needle,
first and second blood collection containers,
first and second auxiliary conduit means respectively attached in fluid communication with said collection containers, and
a fluid manifold interconnecting said primary conduit means and said first and second auxiliary conduit means, said manifold including
a main passage having a portion attached in flow communication with said primary conduit means and a portion normally open to communication with the atmosphere and accommodating attachment to a recipient set for conducting fluids into said main passage,
a pair of branch passages joining said main passage in a spaced-apart relationship and being attached in flow communication with a respective one of said first and second auxiliary conduit means, and
a plug removably insertable through said normally open portion of said main passage and into the interval between the junctions of said spaced apart branch passages with said main passage, said plug including a cap portion which, when said plug is inserted, sealingly occupies and closes said normally open portion, said plug further including a stem portion which, when said plug is inserted, sealingly occupies and closes said main passage in said interval for blocking flow communication between said branch passages through said main passage.

2. A blood collection assembly according to claim 1 wherein, when said plug is removably inserted into said open portion of said main passage, said stem portion blocks flow communication through said main passage between said primary conduit means and one of said branch passages while affording flow communication through said main passage between said primary conduit means and the other one of said branch passages.

3. A blood collection assembly according to claim 1 or 2
wherein one of said branch passages joins said main passage at a position generally adjacent to said normally open portion, and
wherein the other one of said branch passages joins said main passage at a position generally adjacent to said portion of said main passage attached to said primary conduit means.

4. A blood collection assembly according to claim 3 wherein each of said branch passages is generally perpendicularly disposed relative to said main passage.

5. A blood collection assembly according to claim 4 wherein said cap portion of said plug includes a tab member facilitating the removal of said cap portion from said normally open portion of said main passage.

6. A blood collection assembly according to claim 4 wherein said main passage includes a portion tapering inwardly away from said normally open portion, and wherein said stem portion of said plug includes a tapered portion corresponding with said inwardly tapering portion of said main passage for interference fit therein when said cap portion is sealingly engaged in said normally open portion.

7. A blood collection assembly according to claim 6 wherein said stem portion of said plug is made of a resiliently compressible material for an interference fit within said main passage.

8. A blood collection assembly according to claim 1 wherein said main passage portion which is attached in flow communication with said primary conduit means comprises a first leg of said main passage, wherein said branch passages join said first leg in said spaced-apart relationship, and wherein said normally open main passage portion comprises a second leg of said main passage and joins said first leg in said interval between said branch passages.

9. A blood collection assembly according to claim 8 wherein said second leg extends in generally a perpendicular direction relative to said first leg.

10. A blood collection assembly according to claim 8 or 9 wherein said branch passages are spaced apart on opposite sides of said first leg.

11. A blood collection assembly according to claim 8 or 9 wherein said branch passages are spaced apart along the same side of said first leg.

12. A blood collection assembly according to claim 8 or 9 wherein said branch passages extend from said first leg at generally acute angles relative thereto.

13. A blood collection assembly according to claim 8 or 9 wherein said branch passages extend generally perpendicularly from said first leg.

14. A blood collection assembly according to claim 1 wherein said branch passages are arcuately spaced apart along said main passage.

15. A blood collection assembly according to claim 1 wherein said branch passages are spaced apart on opposite sides of said main passage.

16. A blood collection assembly according to claim 1 wherein said branch passages are spaced apart along the same side of said main passage.

17. A blood collection assembly according to claim 1 wherein said branch passages extend from said main passage at generally acute angles relative thereto.

18. A blood collection assembly according to claim 1 wherein each of said branch passages extend generally perpendicularly from said main passage.

* * * * *